United States Patent
LaRose et al.

(10) Patent No.: US 7,972,122 B2
(45) Date of Patent: Jul. 5, 2011

(54) MULTIPLE ROTOR, WIDE BLADE, AXIAL FLOW PUMP

(75) Inventors: Jeffrey A. LaRose, Parkland, FL (US); Charles R. Shambaugh, Jr., Coral Gables, FL (US)

(73) Assignee: Heartware, Inc., Miami Lakes, FL (US)

( * ) Notice: Subject to any disclaimer, the term of this patent is extended or adjusted under 35 U.S.C. 154(b) by 667 days.

(21) Appl. No.: 11/118,551

(22) Filed: Apr. 29, 2005

(65) Prior Publication Data

US 2006/0245959 A1  Nov. 2, 2006

(51) Int. Cl.
  *F04B 35/04*  (2006.01)
(52) U.S. Cl. .................................. 417/356; 417/423.5
(58) Field of Classification Search .................. 417/355, 417/356, 423.1, 423.14, 423.5, 423.7; 416/236 R; 415/900
  See application file for complete search history.

(56) References Cited

U.S. PATENT DOCUMENTS

| | | | |
|---|---|---|---|
| 0,050,714 A * | 10/1865 | Jacob | 416/227 R |
| 2,941,477 A | 6/1960 | Dalton | |
| 3,426,721 A * | 2/1969 | Justinien | 440/48 |
| 3,608,088 A | 9/1971 | Dorman | |
| 3,685,059 A | 8/1972 | Bokros et al. | |
| 4,437,815 A | 3/1984 | McMullen | |
| 4,589,822 A | 5/1986 | Clausen et al. | |
| 4,595,390 A | 6/1986 | Hakim et al. | |
| 4,615,691 A | 10/1986 | Hakim et al. | |
| 4,625,712 A | 12/1986 | Wampler et al. | |
| 4,642,036 A | 2/1987 | Young | |
| 4,688,998 A | 8/1987 | Olsen et al. | |
| 4,753,221 A | 6/1988 | Kensey et al. | |
| 4,817,586 A | 4/1989 | Wampler et al. | |
| 4,846,152 A | 7/1989 | Wampler et al. | |
| 4,906,229 A | 3/1990 | Wampler et al. | |
| 4,908,012 A | 3/1990 | Moise et al. | |
| 4,919,647 A | 4/1990 | Nash | |
| 4,927,407 A | 5/1990 | Dorman | |
| 4,944,722 A | 7/1990 | Carriker et al. | |
| 4,957,504 A | 9/1990 | Chardack | |
| 4,994,078 A | 2/1991 | Jarvik | |
| 4,995,857 A | 2/1991 | Arnold | |

(Continued)

FOREIGN PATENT DOCUMENTS

GB  1067054  4/1967

OTHER PUBLICATIONS

U.S. Appl. No. 11/003,810, LaRose et al.

(Continued)

*Primary Examiner* — William H Rodríguez
*Assistant Examiner* — Dnyanesh Kasture
(74) *Attorney, Agent, or Firm* — John P. White; Cooper & Dunham LLP (57) ABSTRACT

A blood pump comprises a pump housing; a plurality of rotors positioned in said housing, each rotor comprising an impeller having a hydrodynamic surface for pumping blood; and a motor including a plurality of magnetic poles carried by each impeller, having motor stators, each including electrically conductive coils located adjacent to or within the housing. At least one of the rotors is adopted to rotate clockwise, and at least one of rotors is adopted to rotate counterclockwise. By this means, stator or stationary blades between the rotors may not be needed.

16 Claims, 7 Drawing Sheets

U.S. PATENT DOCUMENTS

| | | | |
|---|---|---|---|
| 5,061,256 | A | 10/1991 | Wampler et al. |
| 5,092,879 | A | 3/1992 | Jarvik |
| 5,112,200 | A | 5/1992 | Isaacson et al. |
| 5,209,650 | A | 5/1993 | Lemieux |
| 5,211,546 | A | 5/1993 | Isaacson et al. |
| 5,290,227 | A | 3/1994 | Pasque |
| 5,290,236 | A | 3/1994 | Mathewson |
| 5,344,443 | A | 9/1994 | Palma et al. |
| 5,376,114 | A | 12/1994 | Jarvik |
| 5,385,581 | A | 1/1995 | Bramm et al. |
| 5,501,574 | A | 3/1996 | Raible |
| 5,527,159 | A | 6/1996 | Bozeman, Jr. et al. |
| 5,588,812 | A | 12/1996 | Taylor et al. |
| 5,613,935 | A | 3/1997 | Jarvik |
| 5,678,306 | A | 10/1997 | Bozeman, Jr. et al. |
| 5,692,882 | A | 12/1997 | Bozeman, Jr. et al. |
| 5,707,218 | A | 1/1998 | Maher et al. |
| 5,713,727 | A | 2/1998 | Veronesi et al. |
| 5,746,709 | A | 5/1998 | Rom et al. |
| 5,776,190 | A | 7/1998 | Jarvik |
| 5,824,070 | A | 10/1998 | Jarvik |
| 5,840,070 | A | 11/1998 | Wampler |
| 5,851,174 | A | 12/1998 | Jarvik |
| 5,888,241 | A | 3/1999 | Jarvik |
| 5,911,685 | A | 6/1999 | Siess et al. |
| 5,924,848 | A | 7/1999 | Izraelev |
| 5,941,813 | A | 8/1999 | Sievers et al. |
| 5,947,892 | A | 9/1999 | Benkowski et al. |
| 5,965,089 | A | 10/1999 | Jarvik et al. |
| 6,015,272 | A | 1/2000 | Antaki et al. |
| 6,058,593 | A | 5/2000 | Siess et al. |
| 6,068,588 | A | 5/2000 | Goldowsky |
| 6,100,618 | A | 8/2000 | Schoeb et al. |
| 6,116,862 | A | 9/2000 | Rau et al. |
| 6,120,537 | A | 9/2000 | Wampler |
| 6,135,729 | A | 10/2000 | Aber |
| 6,139,497 | A | 10/2000 | Amemiya et al. |
| 6,155,969 | A | 12/2000 | Schima et al. |
| 6,176,822 | B1 | 1/2001 | Nix et al. |
| 6,200,260 | B1 | 3/2001 | Bolling |
| 6,227,797 | B1 | 5/2001 | Watterson et al. |
| 6,227,820 | B1 | 5/2001 | Jarvik |
| 6,234,635 | B1 | 5/2001 | Seitzinger et al. |
| 6,234,772 | B1 | 5/2001 | Wampler et al. |
| 6,234,998 | B1 | 5/2001 | Wampler |
| 6,244,835 | B1 | 6/2001 | Antaki et al. |
| 6,247,892 | B1 | 6/2001 | Kazatchkov et al. |
| 6,250,880 | B1 | 6/2001 | Woodard et al. |
| 6,254,359 | B1 | 7/2001 | Aber |
| 6,299,575 | B1 | 10/2001 | Bolling |
| 6,306,116 | B1 | 10/2001 | Hancock |
| 6,368,083 | B1 | 4/2002 | Wampler |
| 6,387,037 | B1 | 5/2002 | Bolling et al. |
| 6,390,969 | B1 | 5/2002 | Bolling et al. |
| 6,428,464 | B1 | 8/2002 | Bolling |
| 6,439,845 | B1 | 8/2002 | Veres |
| 6,447,265 | B1 | 9/2002 | Antaki et al. |
| 6,447,266 | B2 | 9/2002 | Antaki et al. |
| 6,527,521 | B2 | 3/2003 | Noda |
| 6,527,699 | B1 | 3/2003 | Goldowsky |
| 6,530,876 | B1 | 3/2003 | Spence |
| 6,595,743 | B1 * | 7/2003 | Kazatchkov et al. ...... 415/171.1 |
| 6,610,004 | B2 | 8/2003 | Viole et al. |
| 6,685,621 | B2 | 2/2004 | Bolling et al. |
| 6,688,861 | B2 | 2/2004 | Wampler |
| 6,716,157 | B2 | 4/2004 | Goldowsky |
| 6,716,189 | B1 | 4/2004 | Jarvik et al. |
| 6,717,311 | B2 | 4/2004 | Locke |
| 6,719,791 | B1 | 4/2004 | Nusser et al. |
| 6,752,602 | B2 * | 6/2004 | Schulte Eistrup et al. .... 417/356 |
| 6,794,789 | B2 | 9/2004 | Siess et al. |
| 6,869,567 | B2 | 3/2005 | Kretchmer |
| 6,889,082 | B2 | 5/2005 | Bolling et al. |
| 7,011,620 | B1 | 3/2006 | Siess |
| 7,021,905 | B2 | 4/2006 | Torrey et al. |
| 7,070,398 | B2 | 7/2006 | Olsen et al. |
| 7,229,258 | B2 | 6/2007 | Wood et al. |
| 2003/0091450 | A1 | 5/2003 | Davis et al. |
| 2004/0241019 | A1 | 12/2004 | Goldowsky |
| 2006/0036127 | A1 | 2/2006 | Delgado, III |
| 2007/0078293 | A1 | 4/2007 | Shambaugh et al. |
| 2007/0100196 | A1 | 5/2007 | LaRose et al. |
| 2010/0069847 | A1 | 3/2010 | Larose et al. |

OTHER PUBLICATIONS

International Search Report issued by the International Searching Authority (ISA/US) on Aug. 20, 2007 in connection with International Application No. PCT/US2005/035964.

Written Opinion of the International Searching Authority issued by the International Searching Authority (ISA/US) on Aug. 20, 2007 in connection with International Application No. PCT/US2005/035964.

Siegenthaler et al., "Mechanical Circulatory Assistance for Acute and Chronic Heart Failure: a Review of Current Technology & Clinical Practice", Journal of Interventional Cardiology, vol. 16, No. 6, 2003, 563-572.

Song et al. "Axial Flow Blood Pumps", ASAIO Journal 2003, pp. 355-364.

Olsen, Don B. "Presidential Address—The History of Continous-Flow Blood Pumps", Artificial Organs 24(6), pp. 401-404.

Humphrey, Bruce "Coatings—Using Parylene for Medical Substrate Coating", www.devicelink.com/ (Jan. 1996) 5 pages.

MMPA Standard No. 0100-00; Standard Specifications for Permanent Magnet Materials, Magnet Material Producers Association, 28 pages.

International Search Report issued by the International Searching Authority (ISA/US) in connection with International Application No. PCT/US2006/21544.

Written Opinion of the International Searching Authority issued by the International Searching Authority (ISA/US) in connection with International Application No. PCT/US2006/21544.

International Preliminary Report On Patentability issued by the International Bureau of WIPO on Apr. 8, 2008 in connection with International Application No. PCT/US2006/21544.

International Search Report issued by the International Searching Authority (ISA/US) in connection with International Application No. PCT/US2005/42495.

Written Opinion of the International Searching Authority issued by the International Searching Authority (ISA/US) in connection with International Application No. PCT/US2005/42495.

International Preliminary Report On Patentability issued by the International Bureau of WIPO on Apr. 8, 2008 in connection with International Application No. PCT/US2005/42495.

Office Action issued Mar. 17, 2008 in connection with U.S. Appl. No. 11/003,810, filed Dec. 3, 2004.

Final Office Action issued Dec. 10, 2008 in connection with U.S. Appl. No. 11/003,810, filed Dec. 3, 2004.

Advisory Action issued Apr. 27, 2009 in connection with U.S. Appl. No. 11/003,810, filed Dec. 3, 2004.

Notice of Allowance issued Aug. 28, 2009 in connection with U.S. Appl. No. 11/003,810, filed Dec. 3, 2004.

Notice of Allowance issued Jan. 12, 2010 in connection with U.S. Appl. No. 11/003,810, filed Dec. 3, 2004.

Office Action issued Sep. 10, 2007 in connection with U.S. Appl. No. 11/243,722, filed Oct. 5, 2005.

Final Office Action issued Jun. 20, 2008 in connection with U.S. Appl. No. 11/243,722, filed Oct. 5, 2005.

Advisory Action issued Oct. 14, 2008 in connection with U.S. Appl. No. 11/243,722, filed Oct. 5, 2005.

Office Action issued Dec. 19, 2008 in connection with U.S. Appl. No. 11/243,722, filed Oct. 5, 2005.

Final Office Action issued Sep. 30, 2009 in connection with U.S. Appl. No. 11/243,722, filed Oct. 5, 2005.

Office Action issued Sep. 22, 2009 in connection with U.S. Appl. No. 11/445,963, filed Jun. 2, 2006.

U.S. Advisory Action issued Jan. 26, 2010 in connection with U.S. Appl. No. 11/243,722, filed Oct. 5, 2005.

Office Action issued Mar. 24, 2010 in connection with U.S. Appl. No. 11/243,722, filed Oct. 5, 2005.

Final Office Action issued Sep. 13, 2010 in connection with U.S. Appl. No. 11/243,722, filed Oct. 5, 2005.
Advisory Action issued Feb. 28, 2011 in connection with U.S. Appl. No. 11/243,722, filed Oct. 5, 2005.
Office Action issued Jan. 19, 2010 in connection with U.S. Appl. No. 11/445,963, filed Jun. 2, 2006.

Final Office Action issued Aug. 16, 2010 in connection with U.S. Appl. No. 11/445,963, filed Jun. 2, 2006.
Notice of Allowance issued Feb. 17, 2011 in connection with U.S. Appl. No. 11/445,963, filed Jun. 2, 2006.

* cited by examiner

MULTIPLE ROTOR, WIDE BLADE, AXIAL FLOW PUMP

BACKGROUND OF THE INVENTION

This discloses a modification of the pump devices disclosed in LaRose et al. U.S. patent application Ser. No. 11/003,810. The modification can also be used with other pumps as well.

The known axial flow pumps for blood have the advantage of narrow width, when compared with radial flow pumps. Axial flow pumps typically have a cylindrical housing with an inlet at one end, an outlet at the opposite end, and a rotor within the housing which has impeller blades attached to the rotor. Thus, as the rotor rotates, the blades add work to the fluid, propelling the fluid through one end of the housing.

A suspension system is provided to maintain the rotor in desired position within the housing, and a motor is provided to spin the rotor. Blood flows between the blades, being propelled through the pump by hydrodynamic forces transferred by the blade surfaces.

The blood then leaves the pump, flowing parallel to the axis of rotation of the rotor. Typically in the prior art, the rotor is suspended by mechanical bearings or bushings, with a rotor shaft protruding through the pump housing to a motor drive mechanism. Magnetic suspension is also known, as in U.S. Pat. Nos. 6,368,083 and 5,840,070.

Typically, axial blood flow pumps have used a thin blade design, with the motor magnets being placed either in the rotor shaft far away from the surrounding stator as in pumps by Jarvik and Incor, or they use small magnets placed within the thin blades, as in the MicroMed pump. Both of these approaches tend to reduce the motor torque capacity and efficiency, and most use mechanical rotor support involving abutting surfaces that move relative to each other in rotation.

In the cited application Ser. No. 11/003,810, a new utilization of wide (thick), blade-like projections on a rotor in an axial flow configuration is provided for a blood pump, to provide a pump which is mechanically wearless, and can have improved torque. Blood pumps, whether internally or externally located, must exhibit low hemolysis, good resistance to thrombosis, adequate system efficiency, and very high reliability for the expected duration of use for the device. Internally located blood pumps are also subject to anatomical compability design constraints, and the need for elimination of mechanical wear and associated failure modes in order to provide successful, long-term, implantable devices. The pump of this invention can achieve the above. Also, the pump can be sealless.

While such a pump of this invention is described in terms of a blood pump, it is also contemplated that the pump might be used for pumping chemically difficult fluids, where a sealless design is highly desirable, and the fluid must be gently handled for various reasons, for example because it is unstable to mechanical stress, causing decomposition and even explosiveness, or because it is another complex, biological fluid besides blood, having critical stability parameters, like blood.

Figure 9:
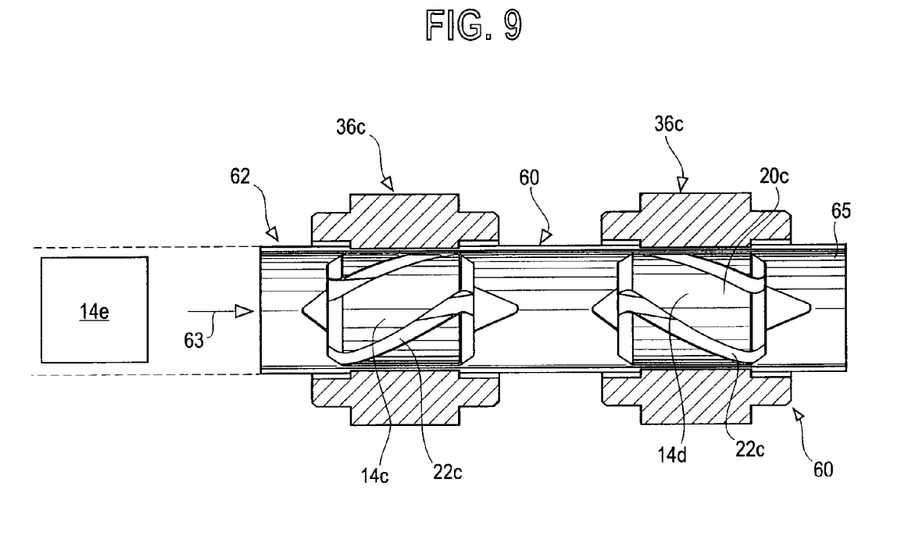
FIG. 9 is a plan view, taken partially in longitudinal section, showing a plurality of blood pumps arranged in series flow, in accordance with this invention, to provide a pump with greater power.

By this present invention, an improved multiple stage blood pump is provided, which gives greater pumping power, constituting a modification of a ganged series of blood pump rotors as shown in FIG. 9 of the previously cited application, with the rotors being in series. Also, a high capacity pump of smaller diameter can be provided in this manner, which is a very significant factor in the case of an implantable pump.

DESCRIPTION OF THE INVENTION

In accordance with this invention, a blood pump is provided which comprises a pump housing, a plurality of rotors positioned in the housing, each rotor comprising an impeller having a hydrodynamic surface for pumping blood, and a motor. The motor includes a plurality of magnetic poles carried by each impeller, to interact with motor stators, each stator including electrically conductive coils located adjacent to or within the housing.

By this invention, at least one of the rotors is adapted to rotate clockwise, and at least one of the rotors is adapted to rotor counterclockwise. Thus, it can be seen that the rotation of the respective rotors is generally independent of each other, and the rotors are preferably spaced from each other.

In some embodiments, the rotors are free of stationary, swirl suppressing blades positioned between them, since the need for such blades can be eliminated by the counterrotating characteristic of the respective rotors. Furthermore, in some embodiments, the rotors are free to rotate at different rates from each other, as driven by their respective motors, although, if desired, the rotation rates of the rotors may be synchronized.

In some embodiments, more than two rotors are present, and adjacent rotors rotate in opposite directions from each other, so that the clockwise rotor or rotors are interspersed with counterclockwise rotating rotors, in a line of series-mounted rotors for driving flow through the pump housing, which is typically cylindrical.

Accordingly, it can be seen that the need for a shaft between the rotors is eliminated. Also, a simplified housing may be used, as opposed to a split housing design that may be required for a traditional, multiple stage pump design. Since a multiple stage blood pump may permit diameter reduction relative to a comparable, single stage pump, this may further allow simplification of device implant procedure, and may significantly reduce patient surgical trauma.

Also, as stated, the need for synchronization between the two motor stators may be lessened or eliminated, since this device will run with a misalignment of drive waveforms of the respective motors, and differing rotation rates for the respective rotors may be actually planned as a condition of normal operation, if desired. Alternatively, the respective, independently rotating rotors may be planned to rotate at similar rates, if desired.

Hydrodynamic bearing surfaces may also be present, being symmetrically located around the impeller. The term "hydrodynamic bearing surfaces" implies that the bearing surface is acting against fluid to impart forces to the rotor, which helps to position the rotor.

In some embodiments, each impeller comprises radially outwardly extending, blade-like projections that define generally longitudinally extending spaces between the projections. The projections are shaped to form curves in the spaces of a shape tending to drive blood in an axial direction as the impeller is rotated. In some embodiments, the spaces collectively have a total width (i.e., the entire sum of the widths of the spaces) that is substantially equal to or less than the collective, total widths of the projections themselves. This measurement is taken at the radial periphery of the rotor.

Thus, the bladelike projections can be much wider, particularly at their peripheries, than in analogous prior art axial flow blood pumps, and the longitudinal spaces or channels between the projections are narrower particularly at the peripheries, than in the prior art. This permits the emplacement of larger motor magnets enclosed inside of the projections, to increase the magnetic flux. Also, the motor air gap can be reduced, when the motor magnets are near the outer tip of each projection, being closer to the motor stator. This increases magnet flux area, which, with the reduced air gap, improves the motor torque capacity and electromagnetic efficiency.

The wide, blade-like projections also preferably have hydrodynamic thrust bearings at radially outer edges of the bladelike projections, with the thrust bearings having sufficient surface area for rotor radial support. The hydrodynamic thrust bearings may work by providing a decreasing flow area in the direction of rotation, and are well known to the art generally, as in U.S. Pat. No. 5,840,070. The external work is provided by the rotor forcing blood flow through a decreased or constricted area created by the hydrodynamic thrust bearings. This results in increased fluid pressure upstream of the constriction, which pressure acts against the surface area and produces a net force for radial support. This hydrodynamic force that is thus created on the outer edges of the rotor projections can resist magnetic forces from the motor and any dynamic, radial shock loading forces.

Figure 5:
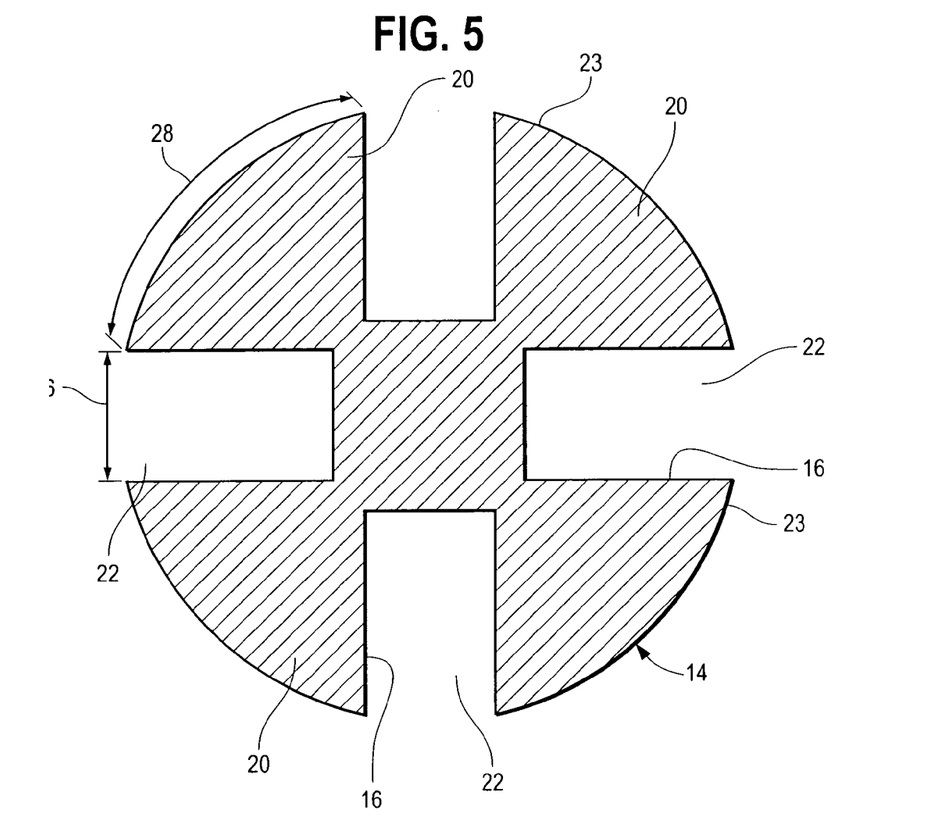
FIG. 5 is a sectional view taken along line 5-5 of FIG. 2, with internal parts omitted.

Typically, the bladelike projections define longitudinally extending spaces between them, with sidewalls having transverse sections that mostly have generally parallel sides, as in FIG. 5.

It is also preferred for the bearings to each define a bearing surface with shrouds carried at ends of the bearing surface, typically at the radially outer face of each hydrodynamic bearing. These bearing shrouds can reduce the amount of end fluid leakage, and can allow the development of higher pressure levels. Fluid leakage can limit the amount of pressure that a hydrodynamic bearing can generate. The reduction of such end leakage to acceptable levels by means of the shrouds can almost double the load carrying capacity for the bearings.

Also, a pressure relief surface, which may be a diverging area downstream of a thrust bearing, can be added to reduce the level of hemolysis of the blood being pumped.

Additionally, the hydrodynamic thrust bearings which are located on the outer periphery of each rotating projection can also be provided with good fluid washing, since centrifugal forces tend to push fluid (blood) toward the outer periphery of the housing interior, providing increased blood flow, which can improve the pump's resistance to thrombosis. Hydrodynamic bearings which are closer to the axis of rotation will have reduced surface washing, resulting in a greater possibility of blood coagulation. Thus, since by this invention, conditions are provided that reduce blood coagulation, a lower amount of anticoagulant may be used with the blood pump and patient, which may result in fewer patient adverse side effects.

Also, at least one magnetic bearing system may be provided, as well as the hydrodynamic bearings, to help to position the rotor in its desired position within the housing. Magnetic bearing systems work by having two sets of magnets that repel each other. One set can be located outside or within the tubular housing, and the other, opposing magnets can be located within the wide, bladelike projections of the rotor.

The magnets mounted in the projections may be permanent magnets. The electric motor used may be of radial flux gap design, so that axial magnetic forces assist in holding the rotor in position.

The rotors do not necessarily require additional supporting structures upstream or downstream thereof, in the circumstance where the axial, magnetic forces and the thrust bearings are sufficient to maintain the rotor in desired position during operation.

The motor design may comprise three phase, brushless DC motors, with the motor stators being positioned outside of the housing that carries the blood, which housing is axially aligned with the rotors. The stator contains the motor windings, and may have a back iron design which is consistent with a typical radial flux gap motor design. Large, permanent magnets may be carried because the projections are thick, to provide a strong electromagnetic coupling, and also it can provide the necessary axial stiffness to maintain the rotor in position.

If desired, each stator can comprise a separate, hermetically sealed motor that slides over a tubular housing into position, and is secured thereto. By this means, system efficiency can be improved, and any eddy current losses can be reduced. Laser welding is one possibility for obtaining a hermetic seal if the stator is built into the housing.

The device controller can run the motor at a set rotational speed, which may be set, for example by the attending physician, or it may follow a physiological control algorithm. Pulse width modulation can also be used for speed control.

The permanent magnets at the periphery of the rotating projections may be covered by peripheral cover caps. These cover caps may also provide an added function by defining weight reduction open spaces such as holes, which may be formed to achieve balance of the rotor.

The housing may comprise a simple tube, with each rotor being slid into place and held there by magnetic attraction to the enveloping stators. The housing may be made of a biocompatible material such as titanium or ceramic. A braised weld ring attached to a non-metallic housing outer surface may be used to secure the motor stator. However, the housing does not have to be a constant diameter tube. For example, it might carry a diverging section in the direction of flow, mated to a rotor having a tapered front section containing a hydrodynamic thrust bearing, for additional protection against axial shock loading. Such alignment of a housing diverging section and the motor design could provide a magnetic, axial preload to help ensure that the rotor maintains its position even if it is normally suspended by magnetic force created between the rotor and the motor stator within a non-magnetic housing.

Thus, a wide-bladed, axial flow pump optionally typically utilizing shrouded hydrodynamic thrust bearings is provided, having significant advantage in the pumping of blood. The motor may be integrated within the rotor's bladelike projections, allowing for a compact device with improved system efficiency. The hydrodynamic thrust bearings on the peripheral, blade-like projection surfaces serve to place the main, wearless suspension system component in a region of good washing for increased resistance to thrombosis. Alternative configurations can exclusively use magnetic bearings, since bearing magnets can easily be incorporated within the wide, blade-like projections, or it may be coupled with a sloped forward section, containing a thrust bearing for increased axial thrust resistance.

Typically with this design, the height of the blade-like projections is greater than in comparable and conventional thin blade designs, to make up for a loss of flow area in the circumferential direction. For example, for heart pump uses, the height of such blades from the axis of rotation to their outer faces may be at least 2 mm, up to typically about 10 mm.

Such a design is more tolerant of flow variations than previous, thin blade designs, since the flow of blood (or other fluid) can more easily adjust to off-design incident angles, in the absence of upstream flow straighteners, than do thinner blades, which tend to be highly tuned to a particular flow condition. Typically, 2-8 of the wider blades of this invention are provided to a single rotor.

Typically, the permanent motor magnets which are located within the wide, blade-like projections may be selected for magnetic properties, length, and cross-sectional area which provides good electromagnetic coupling with the stator. Because of the large dimensions of the blade-like projections, this particular design becomes easier to effect.

The preferred configurations are "sealless" since the rotor is driven by the motor stators separated from the rotor through a sealed, typically tubular housing.

The hydrodynamic thrust bearings near the leading and/or trailing edge portions of the rotor may be sloped to provide both radial and axial support, and may be useful to increase the device resistance to shock loading. A single, hydrodynamic thrust bearing can be used on the outer surface of each blade-like projection. Alternatively, separate bearings could be used in the leading edge region, the rotor mid-section, and/or the trailing edge region respectively. Typically, hydrodynamic thrust bearings can be placed near the leading edge and near the trailing edge, for rotor stability. The hydrodynamic bearing can be installed perpendicular to the axis of rotation. Also they may be flow aligned in a helix fashion, to improve surface washing as they operate. An optional pressure relief surface downstream of the bearing to reduce hemolysis may also be provided to each bearing if appropriate. This comprises a slightly diverging section to decrease the flow velocity in the direction of rotation, downstream of the hydrodynamic bearing.

Alternatively, magnetic bearings may be used to replace the hydrodynamic thrust bearings, to provide an all magnetic system, if desired. These magnetic bearings could be positioned either forward or aft of the motor magnets.

Unlike designs using thinner blades, upstream and downstream struts which serve as flow straighteners and diffusers are not typically required in devices in accordance with this invention. The absence of these upstream and downstream flow straighteners permits a simpler mechanical design, with fewer axial tolerance concerns associated with the placement of these flow straighteners or diffusers. Also, in the absence of the flow straighteners and diffusers, the device tolerance to off design conditions is increased, by allowing the flow to condition itself prior to entering or leaving the rotor. This reduces hemolysis and improves resistance to thrombosis for blood pump applications.

As previously stated, the pumps in accordance with this invention can also be used for other fluids, for example other biological fluids, or other critical fluids of chemical processes and the like.

Alternatively, the desirable, wide blade-like projection-using pump may be utilized with a mechanical pivot bearing rotor suppression system for greater axial constraint, while taking advantage of the greater motor efficiency of the wider, blade-like projections in accordance with this invention.

Typically, one specific blood pump embodiment would be a rotor having four blade-like projections placed within a continuous, straight housing tube, with the motor being located outside of the housing. The blade-like projections would be designed to have a hydrodynamic thrust bearing near the leading and trailing edges of each projection. The device could be free of upstream and downstream support structures. The motor could be a toroidal, three phase, and wye connected design, in one preferred embodiment. If such a device is being designed for a permanent heart ventricular assist device, it could be a cylindrical device having a 10 millimeters outer diameter and 20 millimeters length, providing flow rates of 2-10 liters per minute against physiologic, differential blood pressures.

Another housing configuration would use a sloped surface for the rotor leading edge, to provide both axial and radial support with the motor axial magnetic stiffness providing axial support. In another embodiment, a similar, sloped surface could be provided on the rotor trailing edge to provide both axial and radial support.

Alternately, a split housing configuration might be provided, with sloped surfaces at both the rotor leading and trailing edges, to provide axial and radial support. Also, the inflow design of the tubular housing could have a converging section for the hydrodynamic thrust bearings to run against, to provide axial and radial support.

The blood pump of this invention might be placed in line with a cannulation system, and with the pump being located within the chest cavity of a patient, such as the pericardial space, abdomen, or subcutaneously near the skin, in a manner similar to pacemaker implantation. Likewise, the pump may be kept external to the body for shorter term vascular circulatory support. Also pumps in accordance with this invention could be used in tandem to provide bi-ventricular support, or even total circulation for the patient in the manner of a full, artificial heart.

Where a smaller diameter blood pump is desired, this can be achieved by the pump of this invention. If desired, stator blades may be provided between the various blood pump stages to de-swirl the flow so that more hydraulic work can be added to the fluid. The stator blades may be of any desired number and typically of a traditional thin blade design. However, if desired, stator blades may carry hydrodynamic thrust or mechanical bearings, and may be used to provide axial support to the rotor. Also, stator blades may be of wide configuration and may include permanent magnets as an integral portion of a magnetic bearing, with other magnets that work with the magnets of the stator blades being located within a rotor shaft or in a rotor blade-like projection. However, the counter-rotating rotors of this invention render the stator blades less necessary, so that they may be omitted in some embodiments.

Also, in a multiple stage pump, single or multiple hydrodynamic thrust bearings may be located on each pump unit of the multiple pump system, or hydrodynamic thrust bearings may be absent from some of the stages if the additional radial support is not required, which of course would increase device efficiency.

Axial alignment of the motor and hydraulic pump stages in a multiple pump may be the same, or leading and trailing motor stages may be located inboard or outboard of the leading and trailing rotor stages, to provide extra axial magnetic support.

As previously stated, upstream and downstream flow straighteners and diffusers are generally not necessary, even in multiple stage units, especially for congealing fluids, such as blood, but they could be included for additional gains and device efficiency or additional axial constraint.

For example, the multiple stage pump unit of this invention having rotors with wide, blade-like projections may comprise an axial flow blood pump which would have two stages for example, each with a rotor having four of the wide projections, placed within a cylindrical housing, with the motor also having stages and located on the outside of the housing in line with the rotor stages. The wide blades would typically have a hydrodynamic thrust bearing near the leading and trailing edges of the blade. No upstream or downstream support structures would generally be necessary. The motor could be a toroidal, three phase, and wye connected design.

A size for a permanent ventricular assist device of multistage configuration as described above could be an outer diameter of six millimeters and a length of 15 millimeters, to provide flow rates of 2-8 liters per minute against physiological differential pressures, as previously described. Also, such a device could be used for a peripheral vessel blood insertion pump, or operating outside of the body. Also, a multiple stage pump, as previously stated, could provide bi-ventricular support and even total artificial heart action.

The pump utilizes hydrodynamic thrust bearings for radial support and the magnetic bearings for axial support, primarily resulting in a system which has no mechanical wear, since no rubbing of solid surfaces takes place in a significant manner.

DESCRIPTION OF SPECIFIC EMBODIMENTS

Referring to FIGS. 1-5, a blood pump 10 is disclosed, comprising a generally cylindrical pump housing 12, which may be made of a non-thrombogenic, rigid, strong material such as titanium and/or a suitable ceramic material. Rotor 14 is positioned within the lumen of pump housing 12, and acts as an impeller, having a hydrodynamic surface, specifically a series of hydrodynamic surfaces 16 that tend to propel blood in an axial direction (as indicated by arrow 18) as rotor 14 is rotated clockwise. Blood pump 10 may be connected to the patient's vascular system.

Rotor/impeller 14 comprises radially outwardly extending, blade-like projections 20 having side walls 16 that define generally longitudinally extending spaces 22 between the projections 20. The projections 20 and their side walls 16 are shaped to form curves in the longitudinally extending spaces 22 which are of a shape tending to drive blood in axial direction 18 as rotor/impeller 14 is rotated (clockwise in the embodiment of FIG. 1).

It will be noted, particularly from FIG. 5, that the longitudinally extending spaces 22 collectively have, adjacent to radially outer periphery 23 at the outer circumference of rotor 14, a collective, total circumferential width that is substantially less than the collective, total circumferential width of the projections 20 at the same radially outer periphery 23. This is illustrated by peripheral width 26, illustrated on one of the longitudinally extending spaces 22 in FIG. 5, when compared with peripheral width 28 of adjacent, blade-like projections 20. Collectively, the four widths 26 of each of the spaces 22 comprise a collective, total width of all four longitudinally extending spaces 22. Four times the distance of arc 28 represents the collective, total width of the four blade-like projections 20. It can be readily seen that the collective total width of the longitudinally extending spaces 22 is substantially less at periphery 23 than the collective, total width of the respective blade-like projections 20, in the embodiment of FIGS. 1-5.

Figure 1:
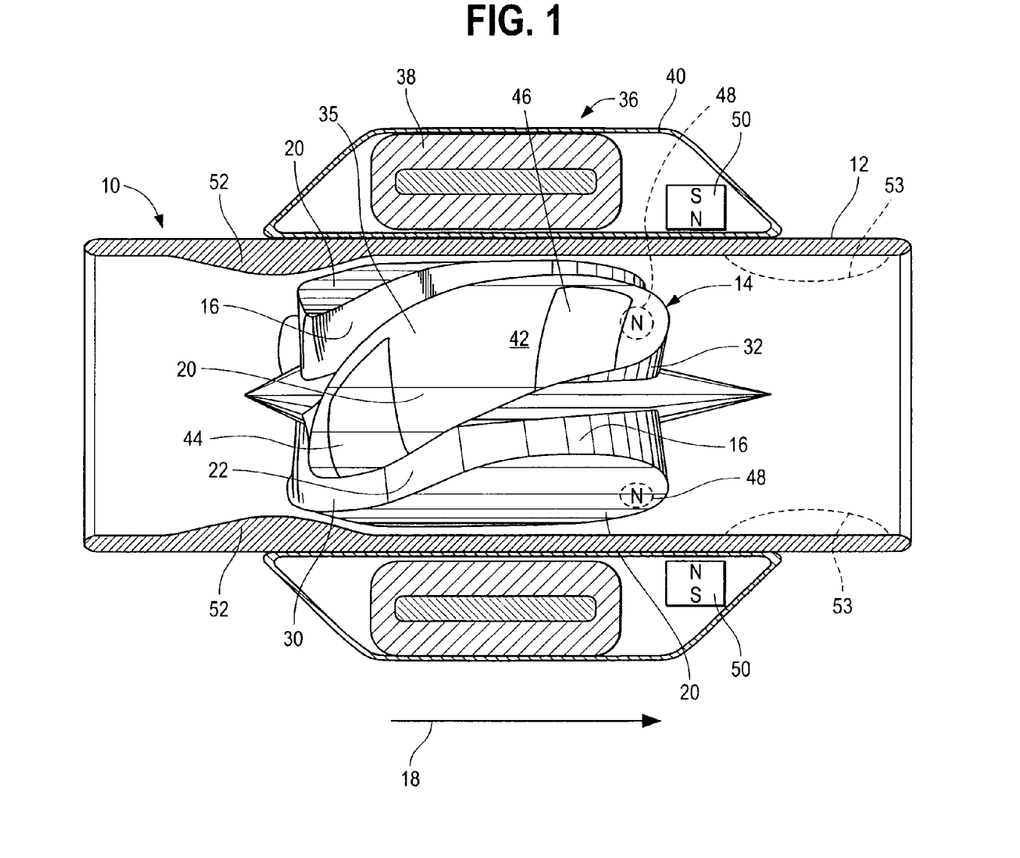
FIG. 1 is an enlarged, longitudinal sectional view of an implantable, sealless, rotary blood pump.

It is preferred for transverse sections (FIG. 5) of longitudinally extending spaces 22 to have generally parallel side walls 16, although it can also be seen from FIG. 1 and other drawings that the overall width of longitudinally extending spaces 22 may vary along their lengths, being particularly somewhat narrower at upstream areas 30, and wider at downstream areas 32, as shown in FIG. 1.

Thus, it can be seen from particularly FIG. 1 that clockwise rotation of rotor 14 will result in a flow of blood within the lumen of housing 12 from left to right in direction 18.

Figure 2:
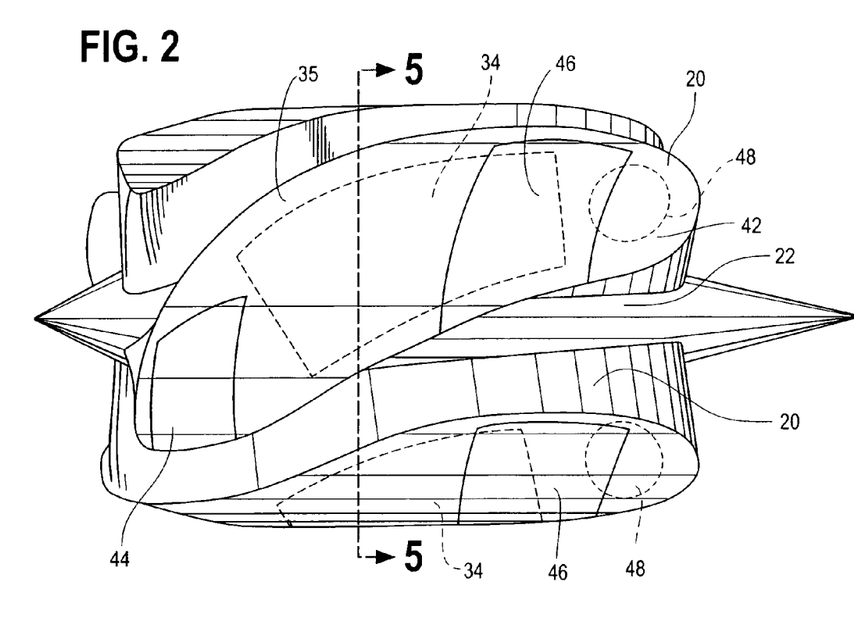
FIG. 2 is a further, enlarged elevational view of the rotor of the pump rotor of FIG. 1.
Figure 3:
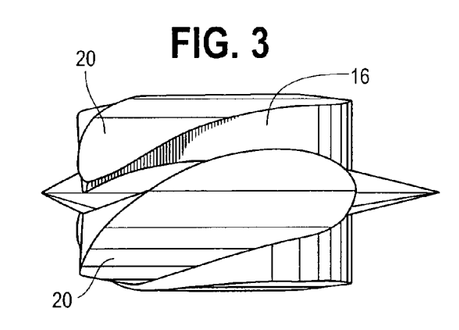
FIGS. 3 and 4 are additional side views of the rotor of FIG. 2 in differing positions.
Figure 4:
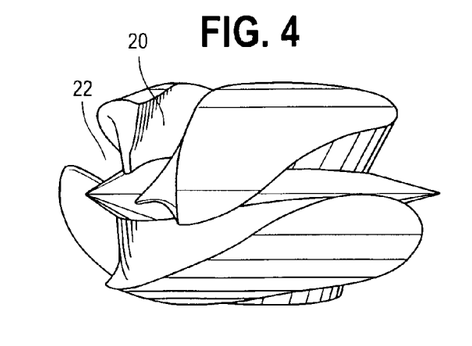

Blood pump 10 further comprises a motor, which includes a plurality of relatively large motor magnets 34 (FIG. 2) respectively carried in the thick, wing-like projections 20 under magnet cover 35 (FIG. 2). The motor also comprises a motor stator 36 (FIG. 1), including an electrically conductive coil 38, within an enclosure 40, which surrounds housing 12 and rotor 14, and serves to rotate rotor 14 by the conventional application of electric power to coil 38, which is converted via magnetic force to torque, causing rotor 14 to rotate clockwise. The specific technology for accomplishing this may be similar to that which is well known in the prior art.

FIGS. 1, 2, 7, and 8 show a radially outer face 42 of a blade-like projection 20, also showing a pair of hydrodynamic bearings 44, 46, which may be carried on magnet cover 35 in the embodiment of FIGS. 1-5, and which use fluid pressure to cause rotor 14 to be centered in the lumen of tubular housing 12 as rotor 14 rotates, in a manner generally shown in FIG. 1, without the need for physical bearings utilizing rubbing, solid surfaces. To facilitate the proper positioning, particularly longitudinal positioning, of rotor 14 within housing 12, a second set of magnets 48, 50 is shown. First magnets 48 (FIG. 2) are mounted in projections 20, under magnet cover 35, adjacent the forward end thereof in this embodiment, with their north poles facing outwardly. Second magnets 50 are carried on tubular housing 12 with their north poles facing inwardly, so that magnetic repulsion takes place between magnets 48 and magnets 50. Of course, the south poles could be directed to face each other in similar manner, to achieve a generally similar effect. Alternatively, magnets 50 may comprise a single, ring magnet or an electromagnetic coil.

Thus, rotor 14 rotates, being held away from the inner wall of housing 12 by hydrodynamic bearings 44, 46 on each of the wing-like projections 20. Longitudinal movement to the right, as in FIG. 1, of rotor 14 is restricted by the action of magnets 48, 50. At the rear of rotor 14, an inner, annular ring 52 is seen to project a bit inwardly from the inner wall cylinder housing 12, to limit the leftward motion of rotor 14. Projection 52 may, if desired, comprise an annular series of spaced projections, or it may comprise a solid ring, with hydrodynamic bearing 44 (FIGS. 2 and 7) serving to prevent contact between rotor 14 and ring 52 as the pump is operating with clockwise rotation of rotor 14. If desired, a similar annular ring 53 may be placed near the other end of housing 12 for similar purpose.

Cover 35 not only carries thrust bearings 44, 46, but it encloses and retains magnets 34, 48.

Of course, it is also within the scope of this invention to design a rotor which can rotate in the counterclockwise direction, making use of the principles and advantages of this invention.

If desired, the stator 36 may comprise a separate, hermetically sealed, coil motor that slides over tubular housing 12 in position, and is secured thereto. Otherwise, stator and coil 38 may be integrally attached to housing 12.

Figure 7:
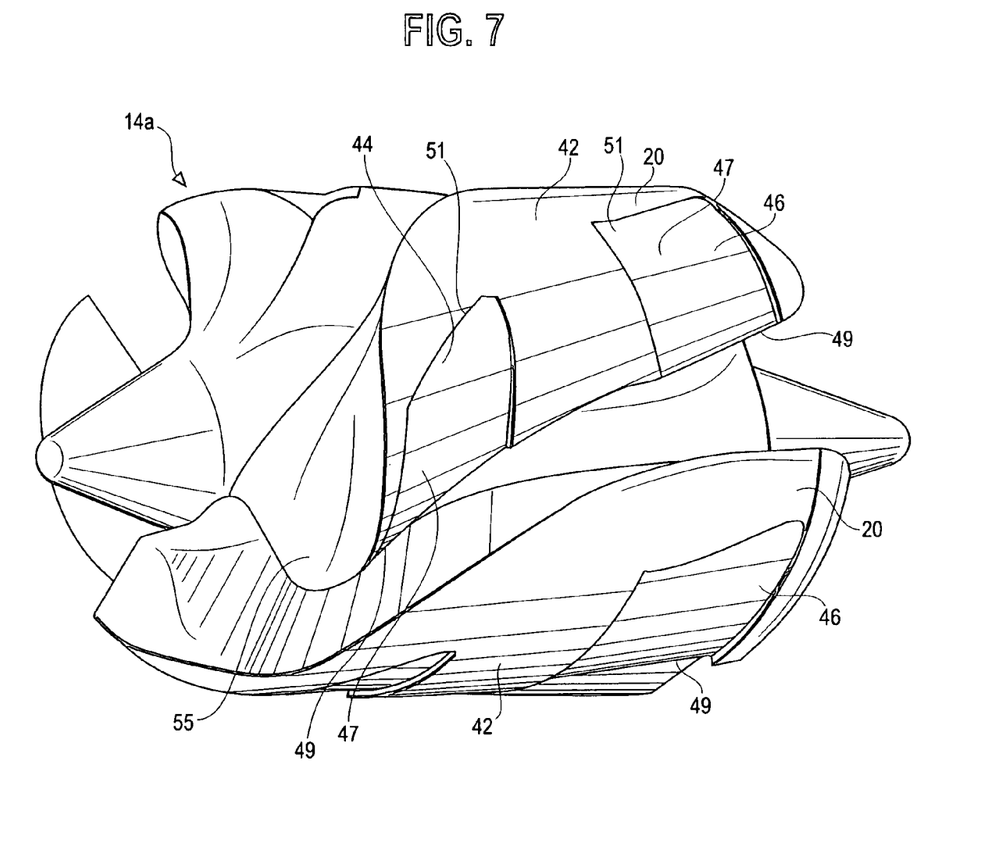
FIG. 7 is an enlarged, rear perspective view of another rotor which is similar to the rotor of FIG. 2.
Figure 8:
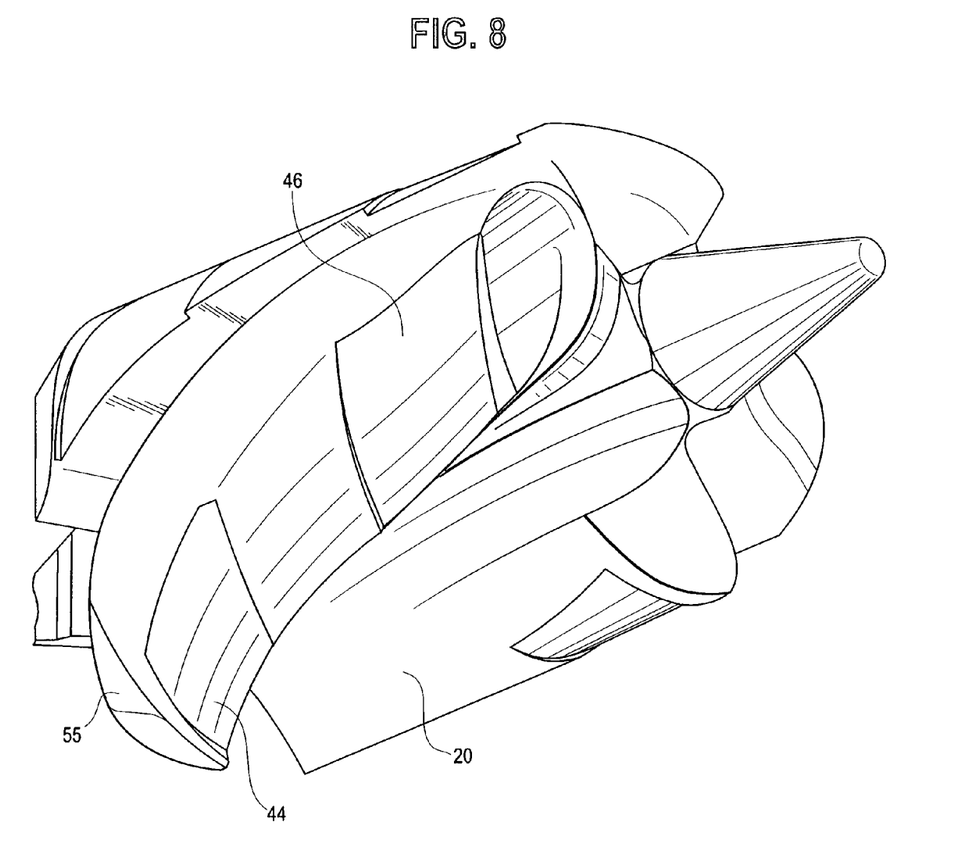
FIG. 8 is a front perspective view of the rotor of FIG. 7.
Figure 8A:
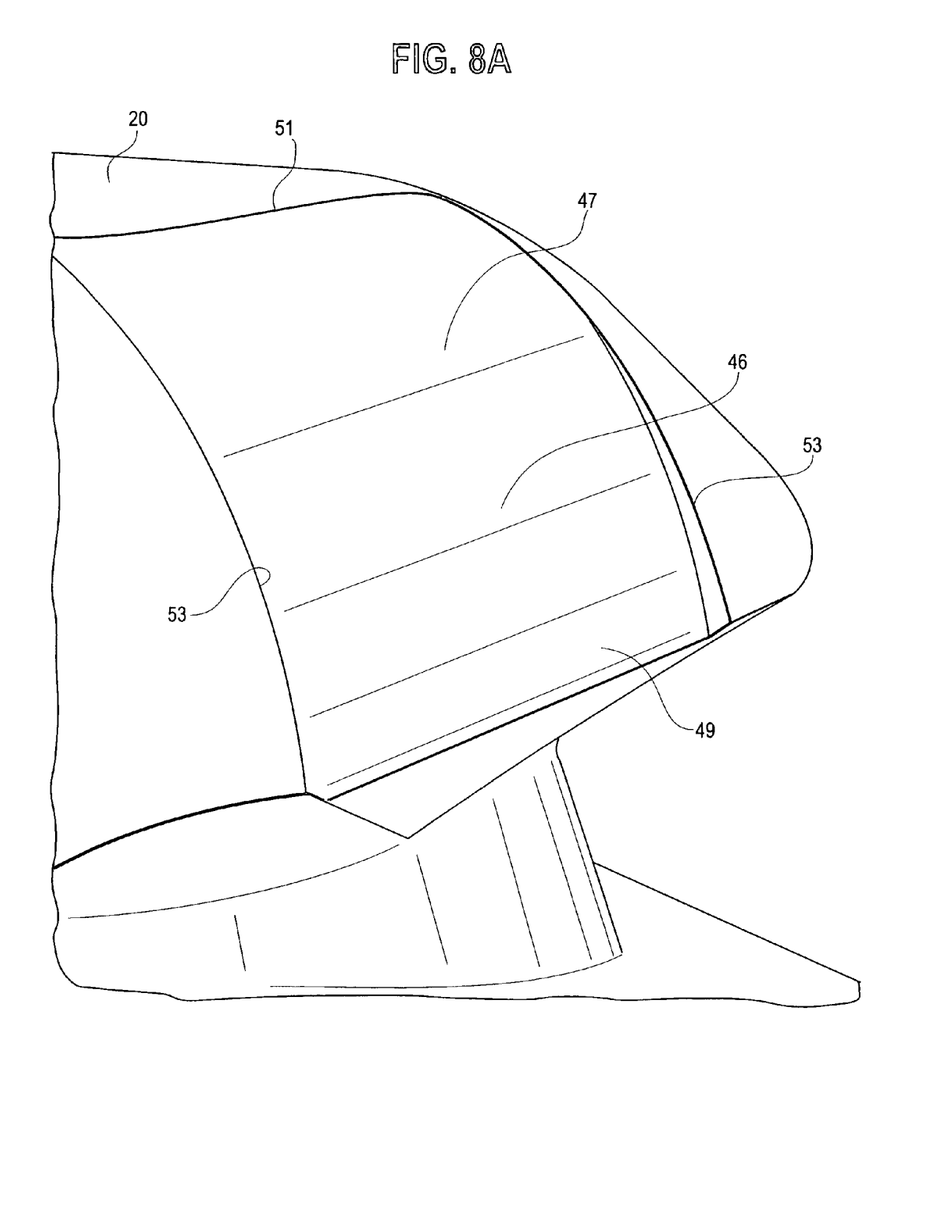
FIG. 8A is an enlarged, fragmentary, perspective view of a portion of the rotor of FIG. 7.

Referring to FIGS. 7, 8, and 8A, details concerning hydrodynamic thrust bearings 44, 46 of rotor 14a are shown in this embodiment, which is similar to the FIGS. 1-5 embodiment except as otherwise stated.

Each of thrust bearings 44, 46 define a recessed, curved outer surface 47 which forms a recessed end portion 49 relative to the outer face 42 of each projection 20, located at the forward end of each bearing 44, 46 from the viewpoint of the (clockwise) spin of the rotor 14a, so that recessed end 49 forms a leading edge of rotation. The recessed surface 47 then tapers in a gradual, curved manner outwardly to the rear end 51 of each thrust bearing 44, 46, at which point, the bearing surface 47 is not recessed, or only very slightly recessed compared with end 49.

Thus, as the rotor rotates, the respective thrust bearings, 44, 46 on each projection 20 scoop blood into a cross-sectional recessed area that decreases going from end 49 to end 51, the effect of this being to pressurize the blood, and to thus repel each projection 20 from the inner wall of housing 12 as the rotor rotates. Since the rotor is spaced from the walls of housing 12, the pressurized blood is released by passing across end 51 and out the sides. Shroud walls 53 (FIG. 8A) connect recessed surface 47 with the rest of projection outer face surface 42.

Bearing 44 operates in a manner similar to bearing 46. In the embodiment of FIGS. 1-5 the bearings 44, 46 also operate in a similar manner Pressure relief zone 55 is provided at the trailing rotary end of each rotating projection 20, to provide pressure relief.

Rotor 14a of FIGS. 7-8A may be used as a substitute for rotor 14. However, rotor 14a may be produced by either machining, molding, or casting a single piece of isotropic, ferromagnetic material, such as compression bonded neodymium or Alnico (aluminum-nickel alloy). After fabrication, the rotor may be treated with a conformal, protective polymer coating of an organic polymer such as Parylene, or silicone, to prevent against oxidation by forming a hermetic seal around the rotor. On top of this, a hard, lubricious protective coating may be applied over the conformal polymer coating, to protect against wear and abrasion. Such coatings may include chromium nitride, titanium-nitride, or other commercially available coatings such as ME92, Med Co 2000, or DLC.

Also, before or after the coating application, the rotor projections 20 may be alternatively magnetized N—S—N—S to form a salient pole rotor magnet so that, contrary to FIG. 1, separate magnets 48 and an outer cover are not present, and each entire rotor projection 20 is appropriately magnetized to operate in the motor of FIG. 1.

Figure 6:
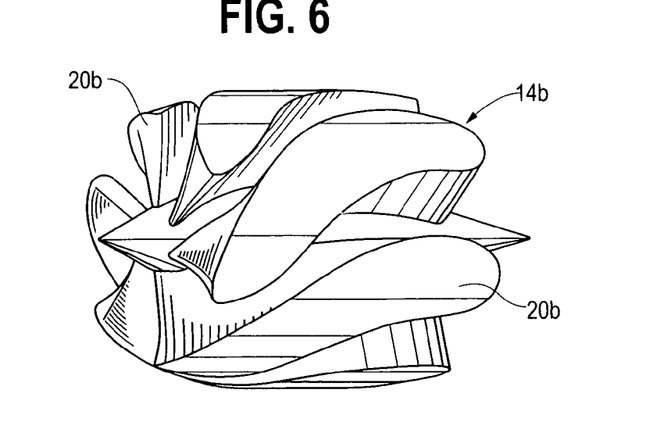
FIG. 6 is a perspective view of an alternative embodiment of a rotor usable in the pump of this invention.

Referring to FIG. 6, another embodiment of a rotor 14b for the blood pump of this invention is disclosed. Rotor 14b is shown to have six blade-like projections 20b, which are generally similar in structure and function to the blade-like projections 20 of the previous embodiments.

Referring to FIG. 9, a plurality of blood pumps 60 are shown, respectively comprising pump rotors 14c, 14d, positioned to pump blood or other fluid through common cylindrical housing 62, pumping the flow in series relationship. The individual rotors 14c, 14d are free, without a shaft connecting them, to rotate independently, and may be of a rotor design as previously described herein, having outwardly extending, blade-like projections 20c, which may be of general design and shape similar to the projections 20 of previous embodiments. By this means, added pumping power can be provided in the form of a multiple stage pump, the rotors being in series connection to provide a high capacity pump of smaller diameter than a single stage pump having comparable power. Thus, the pump of FIG. 9 exhibits significant advantages as to implantability into a patient. The individual pump units 14c, 14d, 14e and the related structure may use the technology disclosed in the previous drawings.

Motor stators 36c each comprise an electrically conductive coil as in the previous embodiments, typically one for each rotor, so that the respective rotors perform in a manner similar to that of the previous embodiments. The stators 36c also may be of a design as previously described, or as otherwise known in the prior art.

The respective rotors 14c, 14d are independently rotatable from each other, being each respectively driven by its own stator 36c, so that the rotation rates of the respective rotors 14c, 14d may be the same as, or different from each other. The rotor 14c on the left is adapted to rotate clockwise, with its respective spaces 22c being appropriately angled to drive blood or other fluid through tubular housing 62 in the direction of arrow 63. Rotor 14d, on the right-hand side of FIG. 9, has slots or spaces 22c that are angled to drive blood in the same direction 63 upon counterclockwise rotation. Thus, the two rotors work together to drive fluid in direction 63, while they counterrotate with respect to each other, each having angled spaces 22c for blood that extend in opposite spiral directions from each other.

In the case where more than two rotors 14 are brought together in series-flow relationship, it is preferred for the respective, adjacent rotors to alternate in their direction of rotation, so that a clockwise rotor such as rotor 14c is adjacent to counterclockwise rotors such as rotor 14d, and optional, added rotor 14e, schematically shown. Rotor 14e would preferably also be a counterclockwise rotor in that circumstance, so that clockwise rotor 14c would be bracketed by counterclockwise rotors 14d, 14e. In the alternative, if rotor 14c were a counterclockwise rotating rotor, then rotors 14d and 14e would be preferably clockwise rotating rotors. If four rotors or more are present in such series relationship, this same, alternating arrangement of direction of rotation is preferably utilized.

Because of the use of rotors which rotate in different directions, there is less need for stationary or stator blades between the rotors to deswirl fluid, since this may be spontaneously accomplished by the counterrotating rotors, permitting more hydraulic work to be added to the fluid.

Depending upon the power applied to the individual stators 36c, the respective rotors may be driven at rotation rates which are similar, or different from each other, as may be desired.

If desired, the forward, outlet end 65 of tubular housing 62 may carry a retention sleeve which provides longitudinal retention of rotor 14d in a mechanical way, so that magnets may be unnecessary for that retention which is provided by the sleeve, although magnets may also be present. Also, such a sleeve may be of reduced diameter, rendering this arrangement suitable as a pediatric version of the pump of this invention.

The above has been offered for illustrative purposes only, and is not intended to limit the scope of the invention of this application, which is as defined in the claims below.

That which is claimed is:

1. A blood pump, comprising:
a pump housing;
a plurality of rotors within said housing aligned along a common rotational axis;
each of said rotors having a plurality of discrete substantially axially directed flow channels which are spaced from each other and extend from one end of said rotor to the other end of said rotor, each of said flow channels having an approximate 90° offset along the axis of said rotor from an inlet entrance to an outlet exit;

each of said rotors having discrete non-channel portions intermediate said flow channels;

said flow channels being in a shape tending to drive blood in said channels through said housing in such axial direction when rotated;

said flow channels collectively having a total width at the radial periphery of the rotor that is equal to or substantially less than the collective total width of the non-channel portions of said rotor at said radial periphery; and a motor comprising a plurality of magnetic poles carried by each of said rotors and a plurality of electromagnetic windings adjacent said magnetic poles for magnetic interaction therewith such that at least two of said rotors may be rotated in opposite directions.

2. The blood pump of claim 1 in which the overall width of said flow channels varies along their lengths.

3. The blood pump of claim 2 in which the flow channels are narrower at the inlet entrance to the flow channels than at the outlet exits from the flow channels.

4. The blood pump of claim 1 in which each of said rotors is axially spaced apart from each other rotor.

5. The blood pump of claim 4 in which said rotors are free of stationary blades positioned between them.

6. The blood pump of claim 1 in which each of said rotors is free to rotate at a different rate relative to each other rotor.

7. The blood pump of claim 1 in which more than two rotors are present and adjacent rotors rotate in opposite directions from each other.

8. The blood pump of claim 1 in which two rotors are present.

9. The blood pump of claim 1 comprising in addition at least one magnetic bearing system to maintain the axial position of each of said rotors within said housing.

10. The blood pump of claim 9 in which said at least one magnetic bearing system comprises permanent magnets mounted in said non-channel portion of each rotor, said motor is of a radial flux gap design type, and axially directed magnetic forces hold the rotor in position.

11. The blood pump of claim 1 in which the motor comprises at least one separate, hermetically sealed unit that slides over said pump housing into position and is secured thereto, said pump housing being tubular.

12. The blood pump of claim 11 in which said housing is cylindrical.

13. The blood pump of claim 1 in which said plurality of rotors positioned in said housing are positioned in series flow, for increased pumping pressure capacity.

14. The blood pump of claim 1 in which said non-channel portions of each rotor have substantially equal peripheral surface areas collectively defining a cylindrical periphery of the rotor; and each of said peripheral surface areas comprises a first tapered surface adjacent an inlet entrance to a flow channel and a second tapered surface adjacent an outlet exit from said flow channel.

15. The blood pump of claim 14 in which each of said first and second tapered surfaces has an entrance portion defining a gap between said tapered surface and said housing, said gap being larger at said inlet entrance than at other portions of said tapered surfaces.

16. The blood pump of 1 in which each of said rotors comprises four of said flow channels.

* * * * *